United States Patent [19]
Cusack et al.

[11] Patent Number: 6,096,889
[45] Date of Patent: Aug. 1, 2000

[54] PROCESS FOR MAKING HIGH PERFORMANCE DYES

[75] Inventors: Kevin P. Cusack, East Greenbush; Louis Molinsek, Glenmont, both of N.Y.

[73] Assignee: BASF Corporation, Southfield, Mich.

[21] Appl. No.: 09/323,346

[22] Filed: Jun. 1, 1999

[51] Int. Cl.$^7$ ...................... C07C 309/29; C07C 309/30; C07C 309/32; C07C 309/35; B07C 309/41
[52] U.S. Cl. .......................... 544/193.2; 562/58; 562/59; 562/60; 562/62; 562/64; 562/68; 562/70; 534/845
[58] Field of Search .......................... 544/193.2; 562/58, 562/59, 60, 62, 64, 68, 70; 534/845

[56] References Cited

U.S. PATENT DOCUMENTS

| | | | |
|---|---|---|---|
| 3,177,207 | 4/1965 | Siegel et al. | 260/240 |
| 4,560,745 | 12/1985 | Weberndoerfer et al. | 534/728 |
| 4,617,381 | 10/1986 | Hinson et al. | 534/689 |
| 4,804,387 | 2/1989 | Degen et al. | 8/641 |
| 5,366,543 | 11/1994 | Ono et al. | 534/728 |
| 5,431,723 | 7/1995 | Bermes et al. | 534/689 |

OTHER PUBLICATIONS

Declaration of Kevin P. Cusak.
Vogel, Arthur, I., Text–Book of Practical Organic Chemistry, 586–589, 1957.

*Primary Examiner*—Richard L. Raymond
*Assistant Examiner*—Venkataraman BalaSubramanian
*Attorney, Agent, or Firm*—Anna M. Budde

[57] ABSTRACT

An aromatic amino sulfonic acid compound is purified by a process including steps of:

(a) dissolving the aromatic amino sulfonic acid compound in aqueous medium having a basic pH;

(b) acidifying the aqueous medium with acetic acid to precipitate the aromatic amino sulfonic acid compound; and (c) removing the precipitated aromatic amino sulfonic acid compound from the aqueous medium.

Using acetic acid in the process results in removal of more impurities and undesirable sulfate and chloride salts to provide an improved material for synthesizing dyes and pigments.

17 Claims, No Drawings

PROCESS FOR MAKING HIGH PERFORMANCE DYES

FIELD OF THE INVENTION

The invention concerns processes for purifying aromatic amino sulfonic acid compounds and to high performance dyes produced from the purified aromatic amino sulfonic acid compounds.

BACKGROUND OF THE INVENTION

Many dyes, as well as pigments, are prepared by a two-step process of diazotization of an aromatic amino compound followed by coupling of the product. In certain applications, such as when the dye is used in an aqueous ink for inkjet printers, it is desirable to exclude, so far as possible, any impurities such as salts. Salt impurities in aqueous inkjet printer inks tend to promote the corrosion of the metal parts of an inkjet printer. In addition, salt impurities in certain aqueous ink compositions may tend to destabilize the ink components, causing the ink components to precipitate.

Hinson et al., U.S. Pat. No. 4,617,381 discloses a process for preparation of Cl Direct Yellow 11 in which the tetrasodium salt is acidified with sulfuric acid to a pH of less than 2.5, then heated. The salt is then neutralized to a pH of 6.0 to 7.5 with an alkanolamine to precipitate the alkanolamine complex. The free acid form is disclosed as having extremely poor filtration characteristics, as the salts formed by neutralization with either sulfuric or hydrochloric acid form a viscous slime that could not be filtered. The alkanolamine complex is reported to have improved stability.

Ono et al., U.S. Pat. No. 5,366,543 discloses preparation of a diazo dye salted with a substituted amine having at least one group of 6 to 12 carbon atoms. Two moles of sec-butylaniline are diazotized and then coupled with 1 mole of di-J acid (bis-(5,5'-dihydroxy-2,2'-naphythyl)amine-7,7'-disulfonic acid) or a similar coupling compound. The water-soluble dye product is salted with an amine having at least one group with 6–12 carbon atoms by mixing an excess of the amine with the water-soluble dye in aqueous solution for 2–5 hours in acidic or neutral atmosphere. When the amine is water-insoluble or has low solubility in water, the salt-formation step is carried out in an organic solvent such as an alcohol followed by addition of the solution into an aqueous acid solution, one example being aqueous acetic acid, to precipitated out the amine-salted dye. The precipitated dye is then filtered and rinsed with water.

Weberndoerfer et al., U.S. Pat. No. 4,560,745 discloses a process for preparing sulfonic acid functional dyes having low electrolyte content. An aqueous solution or suspension of the dyes is mixed with a water insoluble amine having 12 to 40 carbon atoms to separate the dye into a lipophilic phase; bringing the pH to less than 5 with an acid, for example sulfuric acid, and mixing the batch thoroughly, separating the phases, and mixing the lipophilic dye phase with a water soluble base and water to produce an aqueous solution of the dye.

Bermes et al., U.S. Pat. No. 5,431,723 discloses a dye preparation that is essentially free of foreign salts. The dye is prepared by diazotizing 4,4'-diaminostilbene-2,2'-disulfonic acid and then coupling with 1-hydroxy-7-aminonaphthalene-3-sulfonic acid in alkaline medium. The coupled product is acidified with hydrochloric or sulfuric acid to precipitate the product dye. The precipitated product is filtered, washed with water or dilute hydrochloric acid, and dried.

While these references generally discuss purification of a dye product, it would be advantageous to have an improved method of producing an amino sulfonic acid compound-based dye by using a purified starting product. Some of the advantages to purifying the aromatic amino sulfonic acid starting material rather than the finished dye are that (1) the dye is often a form that is difficult to filter and wash, such as a tar-like lake; (2) there is less material that must be purified for the amino- and sulfonic acid-containing starting material as compared to the coupled dye; (3) material loss in the dye purification step is more expensive; and (4) there is no organic in the waste stream that would need more expensive disposal means.

SUMMARY OF THE INVENTION

According to the invention, an aromatic amino sulfonic acid compound is purified by a process including steps of:

(a) dissolving the aromatic amino sulfonic acid compound in aqueous medium having a basic pH;

(b) acidifying the aromatic amino sulfonic acid compound solution with acetic acid to precipitate the aromatic amino sulfonic acid compound; and (c) removing the precipitated aromatic amino sulfonic acid compound from the aqueous medium.

It has been discovered that, while various acids are used for the purification of dyes as described above, acetic acid provides a marked and unexpected advantage in the purification of amino sulfonic acid compounds such as diamino stilbene disulfonic acid compounds that are used as starting materials for dyes and pigments.

DETAILED DESCRIPTION OF THE INVENTION

Compounds suitable for use in the process of the invention are aromatic compounds having one or more amine groups, preferably primary amine groups, and one or more sulfonic acid groups. The aromatic amino sulfonic acid compound has at least one aromatic ring and may have multiple rings. When the aromatic amino sulfonic acid compound has multiple aromatic rings, the aromatic rings can be fused or bridged. Examples of bridged aromatic rings include, without limitation, those bridged by an alkylene group (e.g., methylene or isopropylene) or by an amine group. In addition to the amine and sulfonic acid groups, the aromatic amino sulfonic acid compound can have other substituents, including, without limitation, alkyl groups and hydroxyl groups.

The amino sulfonic acid containing compound is dissolved in aqueous medium having a basic pH. Preferably, the aqueous medium has a pH of at least about 10. In a preferred embodiment the pH of the aqueous medium is adjusted to be from about 10 to about 12. The aqueous medium preferably contains water and a base such as sodium hydroxide, although the medium may contain other materials that would not interfere with the purification process.

The aqueous medium may be heated slightly, for instance to about 45 to 50° C., to obtain a complete solution of the aromatic amino sulfonic acid compound. The solution may be filtered if desired to remove insoluble impurities.

After the aromatic amino sulfonic acid compound has been completely dissolved, the compound is acidified with acetic acid. The pH of the aqueous medium is preferably brought within the range of about 4.5 to about 5.5, more preferably a range of about 4.8 to about 5.1. The aromatic amino sulfonic acid compound should be essentially completely precipitated by the acetic acid. By "essentially completely precipitated" it is meant that the amount of the aromatic amino sulfonic acid compound remaining in the aqueous medium is less than about 2%, preferably less than about 1%, and even more preferably less than about 0.75% by weight of the total weight of the aromatic amino sulfonic acid compound. If more aromatic amino sulfonic acid compound remains in the aqueous phase than desired, additional acetic acid can be added incrementally to achieve more complete precipitation.

The precipitated aromatic amino sulfonic acid compound is separated from the aqueous medium by filtration. The collected solid material is washed with warm water. The water is advantageously at a temperature of at least about 35° C. A convenient temperature range for the wash water is from about 35 to about 45° C. or, more preferably from about 35 to about 40° C. The precipitated aromatic amino sulfonic acid compound is washed with the warm water until the conductivity of the filtrate indicates that essentially all of the soluble salts have been removed. Typically, the washing may be continued until the filtrate has a conductivity of less than about 500 micromhos, and preferably a conductivity of less than about 400 micromhos.

The precipitated aromatic amino sulfonic acid compound recovered preferably has a concentration of sulfate ion of less than about 400 ppm and more preferably less than about 200. The precipitated aromatic amino sulfonic acid compound recovered preferably has a concentration of chloride ion of less than about 100 ppm and more preferably less than about 80 ppm.

The purified aromatic amino sulfonic acid compound is advantageously used in the production of a pigment or dye compound by a two-step process of diazotization followed by coupling of the product. A purified aromatic amino sulfonic acid compound may be the diazotized compound, the coupler, or both.

Examples of suitable aromatic amino sulfonic acid compounds for diazotization include, without limitation, diamino stilbene disulfonic acids, including 4,4'-diaminostilbene-2,2'-disulfonic acid; bis-triazinyl-aminostilbenedisulfonic acids, including unsubstituted or alkoxy or amino substituted bis-triazinyl-4,4'-diaminostilbene-2,2'-disulfonic acid compounds; sulfanilic acid; amino benzene sulfonic acids, such as 1-amino-2-methyl-4-benzenesulfonic acid; amino-azobenzene sulfonic acids, such as 4-amino-azobenzene-4'-sulfonic acid; and so on.

The diazotized compound may be coupled using a conventional coupling process. Examples of compounds known to be suitable couplers include, without limitation, β-napthol, gamma acid (7-amino-1-hydroxynaphthalene-3-sulfonic acid), H-acid (8-amino-1-hydroxynaphthalene-3,6-disulfonic acid), I-acid, J-acid, di-J acid (bis-(5,5'-dihydroxy-2,2'-naphthyl)amine-7,7'-disulfonic acid), 2-hydroxy-3-methylbenzoic acid, and so on.

The dyes produced according to the invention may be used in ink jet printer inks where the absence or extremely low levels of salt impurities is beneficial because of the tendency of such salts to corrode the metallic parts of the ink jet printer.

The invention is further described in the following example. The example is merely illustrative and does not in any way limit the scope of the invention as described and claimed. All parts are parts by weight unless otherwise noted.

EXAMPLE 1

A suitable container is charged with 130 grams of water. While stirring, 15.4 grams of caustic (39% aqueous sodium hydroxide, 0.15 moles) is added slowly. Next, 30 grams (0.081 mole) of 4,4'-diaminostilbene-2,2'-disulfonic acid having a purity of 97%, 1320 ppm sulfate, and 240 ppm chloride is added with high stirring. Stirring is continued for about 10 to 15 minutes. The pH is then adjusted to 10–12, if necessary and the mixture is heated to about 45 to 50° C. to obtain a complete solution.

The solution is then acidified with 20 grams (0.33 mole) of acetic acid. The acidified solution is stirred for 30 to 35 minutes, at which time the pH should be in the range of from about 4.8 to about 5.1 and the 4,4'-diaminostilbene-2,2'-disulfonic acid should be completely precipitated, leaving less than about 0.7% by weight of the 4,4'-diaminostilbene-2,2'-disulfonic acid in the aqueous phase. The aqueous phase can be analyzed for the presence of the 4,4'-diaminostilbene-2,2'-disulfonic acid, and additional acetic acid is added in increments of one gram, if necessary, with additional stirring, to remove additional 4,4'-diaminostilbene-2,2'-disulfonic acid.

The mixture is filtered. The collected 4,4'-diaminostilbene-2,2'-disulfonic acid is washed with 400 grams water at 35 to 40° C. The wash with 35–40° C. water is repeated as necessary until the conductivity of the filtrate is less than about 400 micromhos. The collected 4,4'-diaminostilbene-2,2'-disulfonic acid is then removed from the filter and dried.

The yield is 86.0%. The 4,4'-diaminostilbene-2,2'-disulfonic acid has a measured purity of 96%, 120 ppm sulfate ion, and 56 ppm chloride ion.

COMPARATIVE EXAMPLE A

A suitable container is charged with 130 grams of water. While stirring, 15.4 grams of caustic (39% aqueous sodium hydroxide, 0.15 moles) is added slowly. Next, 30 grams (0.081 mole) of 4,4'-diaminostilbene-2,2'-disulfonic acid having a purity of 97%, 1320 ppm sulfate, and 240 ppm chloride is added with high stirring. Stirring is continued for about 10 to 15 minutes. The pH is then adjusted to 10–12, if necessary and the mixture is heated to about 45 to 50° C. to obtain a complete solution.

The solution is then acidified with 21.5 grams (0.19 mole) of hydrochloric acid. The acidified solution is stirred for 30 to 35 minutes, at which time the pH should be in the range of from about 4.8 to about 5.1 and the 4,4'-diaminostilbene-2,2'-disulfonic acid should be completely precipitated, leaving less than about 0.7% by weight of the 4,4'-diaminostilbene-2,2'-disulfonic acid in the aqueous phase. The aqueous phase can be analyzed for the presence of the 4,4'-diaminostilbene-2,2'-disulfonic acid, and additional hydrochloric acid is added in increments of 0.5 gram, if necessary, with additional stirring, to remove additional 4,4'-diaminostilbene-2,2'-disulfonic acid.

The mixture is filtered. The collected 4,4'-diaminostilbene-2,2'-disulfonic acid is washed with 400 grams water at 35 to 40° C. The wash with 35–40° C. water is repeated as necessary until the conductivity of the filtrate is less than about 400 micromhos. The collected 4,4'-diaminostilbene-2,2'-disulfonic acid is then removed from the filter and dried.

The yield is 86.5%. The 4,4'-diaminostilbene-2,2'-disulfonic acid has a measured purity of 96.5%, 466 ppm sulfate ion, and 3459 ppm chloride ion.

COMPARATIVE EXAMPLE B

A suitable container is charged with 130 grams of water. While stirring, 14.7 grams of caustic (39% aqueous sodium hydroxide, 0.15 moles) is added slowly. Next, 29.5 grams (0.08 mole) of 4,4'-diaminostilbene-2,2'-disulfonic acid having a purity of 97%, 1320 ppm sulfate, and 240 ppm chloride is added with high stirring. Stirring is continued for about 10 to 15 minutes. The pH is then adjusted to 10–12, if necessary and the mixture is heated to about 45 to 50° C. to obtain a complete solution.

The solution is then acidified with 19.7 grams (0.20 mole) of sulfuric acid. The acidified solution is stirred for 30 to 35 minutes, at which time the pH should be in the range of from about 4.8 to about 5.1 and the 4,4'-diaminostilbene-2,2'-disulfonic acid should be completely precipitated, leaving less than about 0.7% by weight of the 4,4'-diaminostilbene-2,2'-disulfonic acid in the aqueous phase. The aqueous phase can be analyzed for the presence of the 4,4'-diaminostilbene-2,2'-disulfonic acid, and additional hydrochloric acid is added in increments of 0.5 gram, if necessary, with additional stirring, to remove additional 4,4'-diaminostilbene-2,2'-disulfonic acid.

The mixture is filtered. The collected 4,4'-diaminostilbene-2,2'-disulfonic acid is washed with 400 grams water at 35 to 40° C. The wash with 35–40° C. water is repeated as necessary until the conductivity of the filtrate is less than about 400 micromhos. The collected 4,4'-diaminostilbene-2,2'-disulfonic acid is then removed from the filter and dried.

The yield is 87.0%. The 4,4'-diaminostilbene-2,2'-disulfonic acid has a measured purity of 93%, 16,000 ppm sulfate ion, and 68 ppm chloride ion.

The Example 1 method of the invention thus produces a product having a marked reduction in corrosive salt impurities over the products of the Comparative Examples A and B methods.

The invention has been described in detail with reference to preferred embodiments thereof. It should be understood, however, that variations and modifications can be made within the spirit and scope of the invention and of the following claims.

What is claimed is:

1. A process for purifying an aromatic amino sulfonic acid compound, comprising the steps of:
   (a) dissolving the aromatic amino sulfonic acid compound in aqueous medium having a basic pH;
   (b) acidifying the aqueous medium with acetic acid to precipitate the aromatic amino sulfonic acid compound; and
   (c) removing the precipitated aromatic amino sulfonic acid compound from the aqueous medium.

2. A process according to claim 1, wherein the aromatic amino sulfonic acid compound is selected from the group consisting of diamino stilbene disulfonic acids, bis-triazinyl-aminostilbenedisulfonic acids, bis-triazinyl-4,4'-diaminostilbene-2,2'-disulfonic acid, alkoxy substituted bis-triazinyl-4,4'-diaminostilbene-2,2'-disulfonic acid compounds, amino substituted bis-triazinyl-4,4'-diaminostilbene-2,2'-disulfonic acid compounds, sulfanilic acid, amino benzene sulfonic acids, 1-amino-2-methyl-4-benzenesulfonic acids amino-azobenzene sulfonic acids, 4-amino-azobenzene-4'-sulfonic acid, gamma acid, and H-acid.

3. A process according to claim 1, wherein the aromatic amino sulfonic acid compound is a diamino stilbene disulfonic acid compound.

4. A process according to claim 3, wherein the diamino stilbene disulfonic acid compound is 4,4'-diaminostilbene-2,2'-disulfonic acid.

5. A process according to claim 1, wherein the aromatic amino sulfonic acid compound is gamma acid.

6. A process according to claim 1, wherein the aromatic amino sulfonic acid compound is H-acid.

7. A process according to claim 1, wherein the precipitated disulfonic acid compound is washed with water that is at a temperature of at least about 35° C. until the collected wash water has a conductivity of less than about 500 micromhos.

8. A process according to claim 7, wherein the water is at a temperature of up to about 45° C.

9. A process according to claim 7, wherein the water is at a temperature of from about 35° C. to about 40° C.

10. A process according to claim 7, wherein the precipitated disulfonic acid compound is washed with water until the collected wash water has a conductivity of less than about 400 micromhos.

11. A process according to claim 1, wherein the aromatic amino sulfonic acid compound has a primary amine group.

12. A process according to claim 1, wherein the pH of step (a) is from about 10 to about 12.

13. A process according to claim 1, wherein the aromatic amino sulfonic acid compound is essentially completely precipitated in step (b).

14. A process according to claim 1, wherein the aqueous medium is brought to a pH of from about 4.5 to about 5.5 in step (b).

15. A process according to claim 1, wherein the aqueous medium is brought to a pH of from about 4.8 to about 5.1 in step (b).

16. A process for purifying an aromatic amino sulfonic acid compound, comprising the steps of:
   (a) dissolving the aromatic amino sulfonic acid compound in aqueous medium having a basic pH;
   (b) acidifying the aqueous medium with acetic acid to precipitate the aromatic amino sulfonic acid compound; and
   (c) removing the precipitated aromatic amino sulfonic acid compound from the aqueous medium, wherein the precipitated aromatic amino sulfonic acid compound is washed with water that is at a temperature of at least about 35° C. until the collected wash water has a conductivity of less than about 500 micromhos and further wherein the washed aromatic amine sulfonic acid compound has a concentration of sulfate ion of less than about 400 ppm and a concentration of chloride ion of less than about 100 ppm.

17. A process according to claim 16, wherein the washed aromatic amino sulfonic acid compound has a concentration of sulfate ion of less than about 200 ppm and a concentration of chloride ion of less than about 80 ppm.

* * * * *